(12) United States Patent
Sudit (10) Patent No.: US 8,954,141 B1
(45) Date of Patent: Feb. 10, 2015

(54) IONTOPHORETIC DEVICE AND A METHOD OF DELIVERY FOR DENTAL APPLICATIONS

(76) Inventor: Michael S. Sudit, Minnetonka, MN (US)

(*) Notice: Subject to any disclaimer, the term of this patent is extended or adjusted under 35 U.S.C. 154(b) by 781 days.

(21) Appl. No.: 12/785,206

(22) Filed: May 21, 2010

Related U.S. Application Data (60) Provisional application No. 61/180,756, filed on May 22, 2009.

(51) Int. Cl.
  *A61N 1/30* (2006.01)
(52) U.S. Cl.
  USPC ............... 604/20; 604/500; 604/501; 433/32
(58) Field of Classification Search
  CPC ............................. A61M 35/003; A61N 1/30
  USPC ............................. 604/20, 501, 500; 433/32
  See application file for complete search history.

(56) References Cited

U.S. PATENT DOCUMENTS 6,006,130 A * 12/1999 Higo et al. ............... 604/20

OTHER PUBLICATIONS

Kostouros et al., "The blocking effect of iontophoretic administration of lidocaine on neurogenic vascular reactions in rat dental pulp," *Eur. J. Oral Sci.* (1996) 104: 577-582.
Gangarosa L.P., "Rationale for local anesthesia of oral mucosa," Iontophoresis in Dental Practice (1983): *Quintessence Publishing Co., Inc.*, Chicago, IL.
Dixit et al., "Iontophoresis—An approach for controlled drug delivery: A review," *Current Drug Delivery* (2007) 4: 1-10.
Kasha et al., "A review of patent literature for iontophoretic delivery and devices," *Recent Patents on Drug Delivery & Formulation* (2008) 2: 41-50.
Gangarosa L.P., Sr., Iontophoresis in Dental Practice (1983): *Quintessence Publishing Co., Inc.*, Chicago, IL.

* cited by examiner

*Primary Examiner* — Edelmira Bosques
(74) *Attorney, Agent, or Firm* — Merchant & Gould, P.C.

(57) ABSTRACT

An iontophoretic dental device that positions electrodes at buccal and lingual gingiva is described herein. The iontophoretic dental device includes an electrode locating member and electrodes that are attached to the electrode locating member. Further described herein is an iontophoretic dental system for simultaneously positioning electrodes at the buccal and lingual gingiva of a tooth on which dental work is performed. The system includes a coupler, lead wires and an iontophoretic dental device that further includes a clamp and electrodes. The electrodes are operatively attached to the clamp. Also described herein is a method of delivering a medicament to teeth or surrounding oral tissues including placing an iontophoretic dental device on buccal and lingual gingiva, the device including a clamp, and applying current to the electrodes.

10 Claims, 9 Drawing Sheets

IONTOPHORETIC DEVICE AND A METHOD OF DELIVERY FOR DENTAL APPLICATIONS

CROSS-REFERENCE TO RELATED APPLICATIONS

This application claims priority from and is related to provisional application 61/180,756 filed on May 22, 2009, which is incorporated herein by reference.

FIELD OF THE INVENTION

The present invention relates generally to iontophoresis for dental applications. The iontophoretic device, system, kit and method of the present invention relate to the delivery of medicament to the gingiva about or proximal to teeth on which dental procedures are to be performed.

BACKGROUND

Iontophoresis is widely accepted procedure used primarily in medical practices and physical therapy settings for the delivery and electro-transport of various medicaments through the skin. The medicaments can include anesthetic solutions or gels and anti-inflammatory solutions or gels, among others.

Iontophoresis uses electrical current to drive polarized solutions (positive and negative). Positively charged solutions/gels/semi-solids are repelled by positive poles and attracted by negative poles, and vice versa, to complete a circuit. The drugs are forced across the skin by electronic repulsion of similar charges. Anionic medicaments may be pushed through the skin by using a negatively charged electrode and cationic medicaments may be pushed through the skin using a positively charged electrode. When used on skin, commonly, a positive solution is placed on a positively charged electrode. A negatively charged electrode is placed at an alternative site on the body and serves as a ground for the circuit. Thus, iontophoresis is the facilitated movement of ions across a membrane under the influence of an externally applied small electrical potential difference. Iontophoresis is localized, non-invasive, convenient and a rapid method of delivering ionized medicament.

Iontophoresis is one approach for delivering drugs as well as therapeutic proteins, peptides, and oligonucleotides. The advantages of iontophoresis are numerous and well known in the art, including improved therapeutic efficacy due to a bypass of hepatic metabolism and the use of drugs with short biological half life due to the direct delivery to the target area. A further advantage is that iontophoresis is a non-invasive method to systematically administer a small amount of drug. Some of the commercially available iontophoretic delivery systems include LIDOSITE, a system to deliver lidocaine and Iomed PHORESOR for the delivery of botulinum.

SUMMARY

The most prevalent reasons for patients' dislike and avoidance of dentists are: fear of pain, fear of the unknown, and fear of needles. The present invention decreases or eliminates the need for needles by delivering medicament to the teeth and surrounding oral tissues using iontophoresis.

A device constructed according to the present invention allows the placement of electrodes on the gingiva about or proximal to teeth on which the dental procedures are to be performed (hereafter "target teeth"). The electrodes may be located at both the lingual and buccal gingiva. The electrodes are attached to an electrode locating member. The electrode locating member positions the electrodes at the lingual and buccal gingiva. The electrodes may comprise a conductive layer and electrolyte reservoir. The electrode is either positively or negatively charged. The electrolyte reservoir may comprise a medicament. The medicament may have a charge similar to the electrode. When a voltage is applied across the electrodes, the medicament is forced away from the electrode and into the gingiva. This allows medication of the teeth and surrounding tissue without using a needle.

A system of the present invention provides the placement of electrodes on the gingiva about or proximal to target teeth. In an embodiment, the system comprises an electrode locating member, electrodes, lead wires, and a coupler. An additional embodiment may further comprise a power source.

A method of the present invention includes placing a device constructed in accordance with the principles of the present invention on the buccal and lingual gingiva of target tooth and applying a voltage. The voltage is supplied by a power source. The resulting current drives the medicament of the electrode into the gingiva.

A kit of the present invention provides a one time or multi-use dental device according to the present invention. An embodiment of the kit includes an electrode locating member and electrodes. Another embodiment includes an electrode locating member, electrodes, lead wires, and a coupler. An additional embodiment further includes medicament. The dental device of the kit is applied to the buccal and lingual gingiva for the delivery of medicament to the gingiva of a target tooth and/or target teeth.

DETAILED DESCRIPTION

Figure 1:
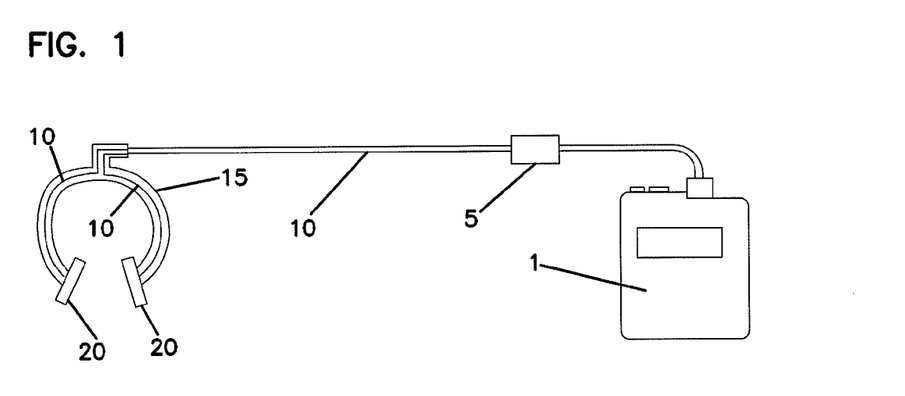
FIG. 1 is a schematic view of an iontophoresis system for dental applications.

Referring now to the drawings wherein like reference numerals designate identical or corresponding parts throughout the several views, an embodiment of an iontophoretic dental system is shown in FIG. 1. The iontophoretic dental delivery system of FIG. 1 comprises a power source 1 electrically connected to electrodes 20 through lead wires 10 and a coupler 5. The electrodes are operatively attached to an electrode locating member. The coupler 5 displayed in this embodiment permits electrical communication between the power source 1 and the electrodes 20.

Figure 2:
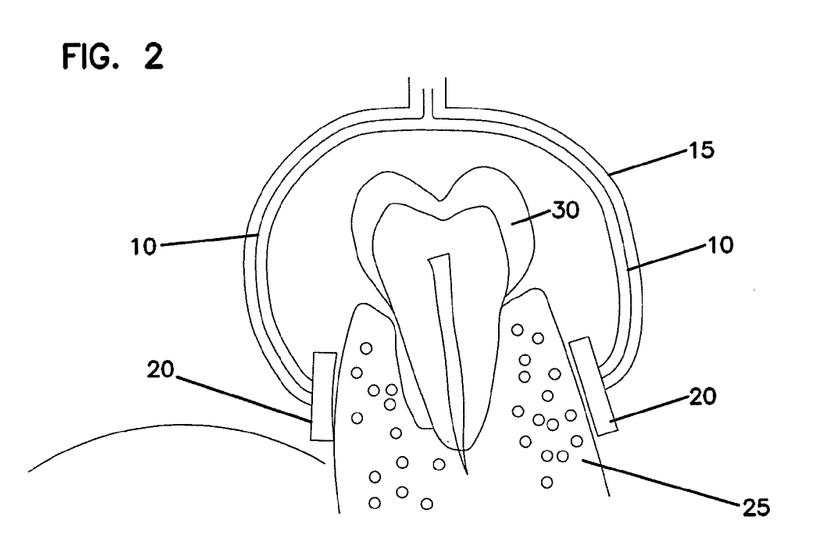
FIG. 2 is a mesial-distal view of an electrode locating member and electrodes where the electrodes are contacting the gingiva surrounding a target tooth.

An embodiment of the iontophoretic dental device in shown in FIG. 2 from a mesial-distal view. The electrode locating member 15 straddles the target tooth 30 and is operatively connected to the electrodes 20. The electrode locating member positions the electrodes at the lingual (tongue) and buccal (cheek) sides of the gingiva 25. The lead wires 10 split at the top of the electrode locating member 15 and follow the arms of the electrode locating member 15 to the connection with the electrodes 20.

Figure 3:
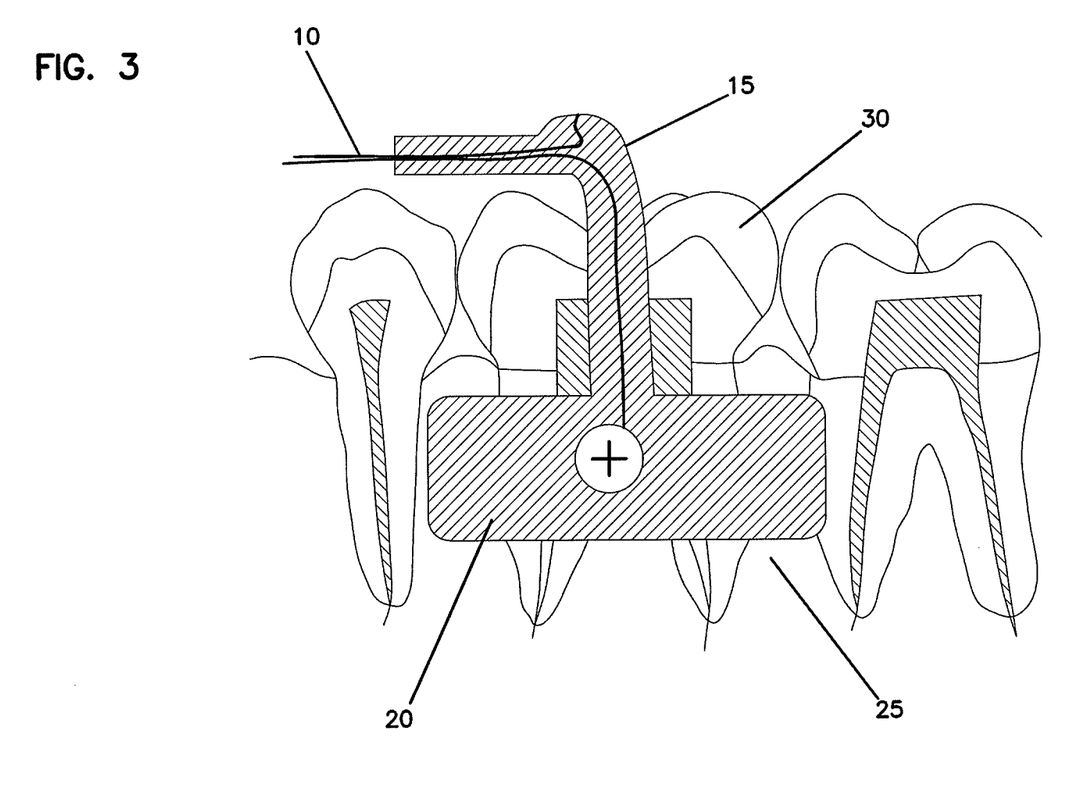
FIG. 3 is a buccal view of an electrode locating member and electrodes of an iontophoresis system where the electrodes contact the gingiva surrounding a plurality of target teeth.

An embodiment of the iontophoretic dental device is shown in FIG. 3 from a buccal view. The electrode locating member 15 is straddling the target teeth 30 and is positioning the electrode 20 at the buccal gingiva 25. The lead wires 10 contact the electrode locating member 15 and split to follow the arms of the electrode locating member 15 to the connection with the electrodes 20. In this embodiment the electrode 20 contacting the buccal gingiva 25 is positively charged.

Figure 4:
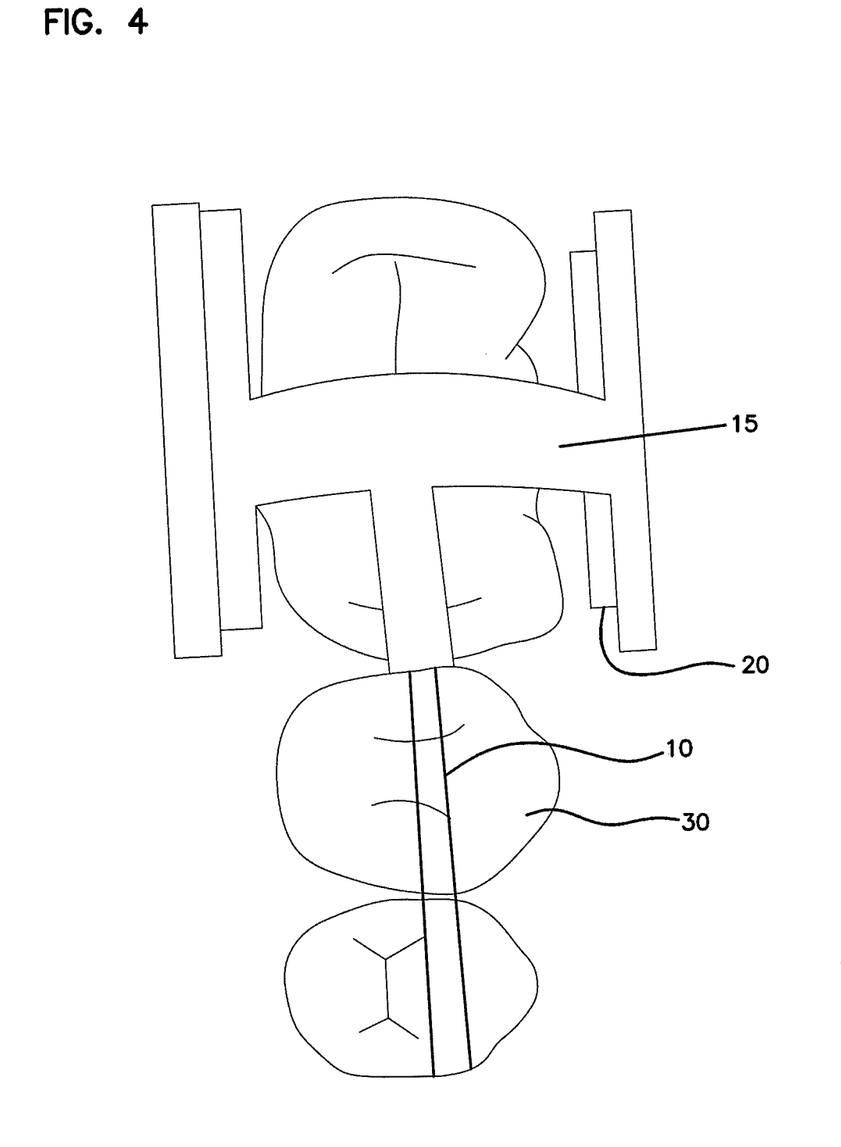
FIG. 4 is an occlusal view of an electrode locating member and electrodes of an iontophoresis system.

An embodiment of the iontophoretic dental device is shown in FIG. 4 from an occlusal view. The electrode locating member 15 is straddling the target teeth 30 and simultaneously positioning the electrodes 20 at the buccal and lingual gingiva. The lead wires 10 run from a coupler (not shown) along the teeth 30 until they meet the electrode locating member 15.

Figure 5:
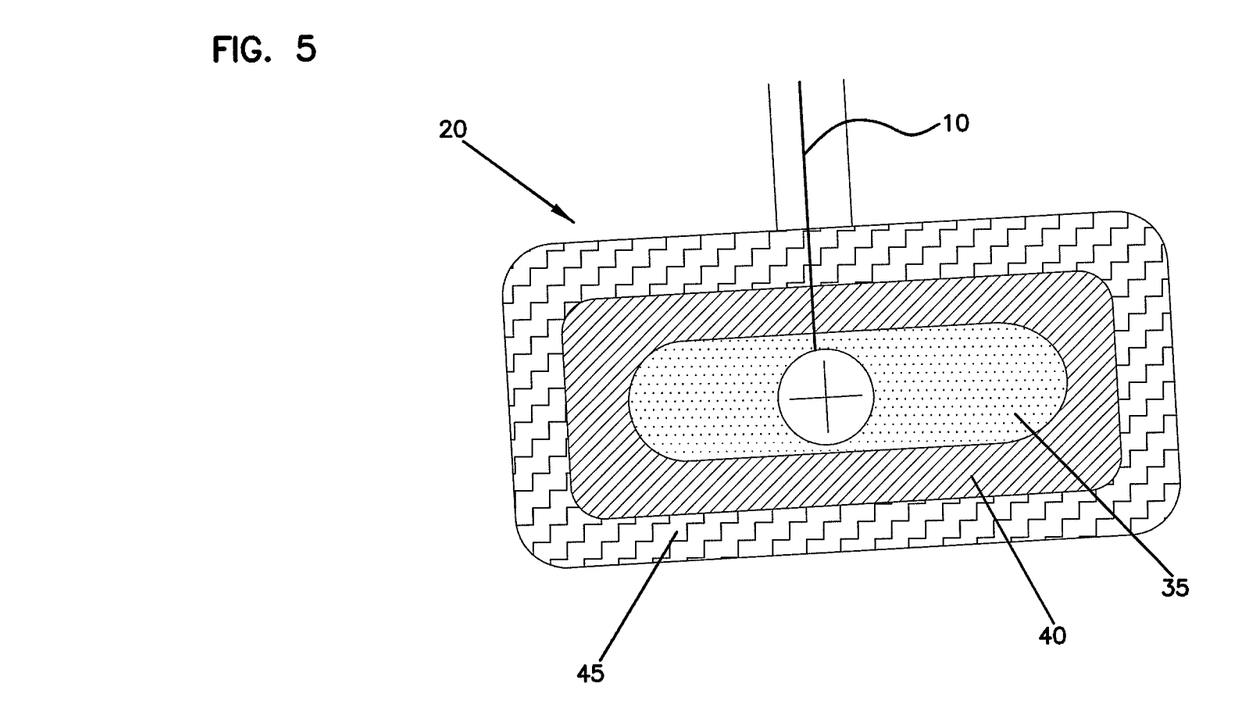
FIG. 5 is a view of the electrode surface that contacts the gingiva when the electrode is held in place by the electrode locating member.

An embodiment of the electrode 20 operatively attached to the electrode locating member is shown in FIG. 5 from an electrode surface view. The lead wires 10 travel along an arm of the electrode locating member to the electrode connection. The electrode comprises a gasket 45, a conductive layer 35, and a membrane 40. In this embodiment, the electrolyte reservoir is on the surface of the conductive layer 35 and both the conductive layer 35 and electrolyte reservoir are positively charged.

Figure 6:
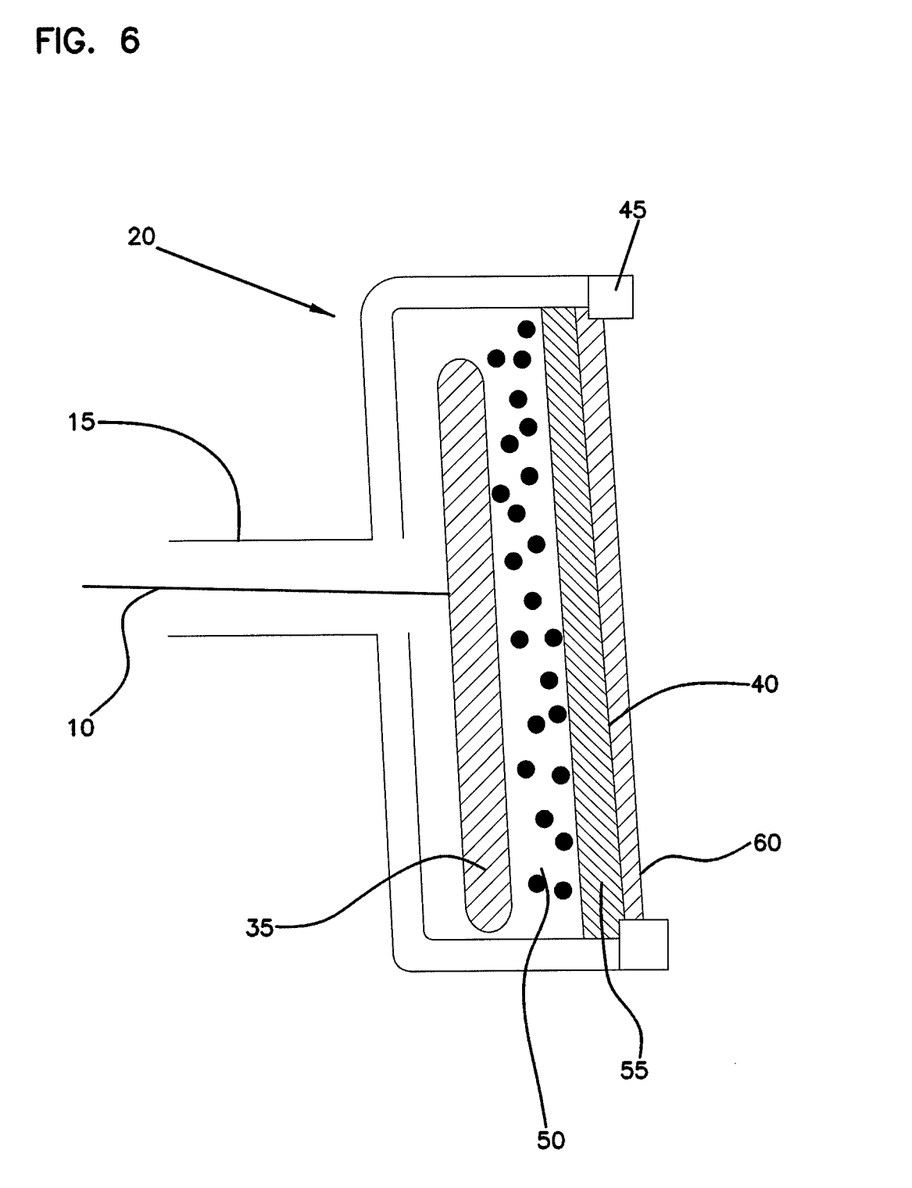
FIG. 6 is a side view of an electrode.

An embodiment of the electrode 20 operatively attached to the electrode locating member 15 is shown in FIG. 6 from an electrode side view. The electrode 20 comprises a conductive layer 35, an electrolyte reservoir 50, and a membrane 40 having multiple layers 55 and 40. The electrode may further comprise a gasket 45. Lead wires 10 travel along the electrode locating member 15 to the connection with the electrode 20.

Figure 7:
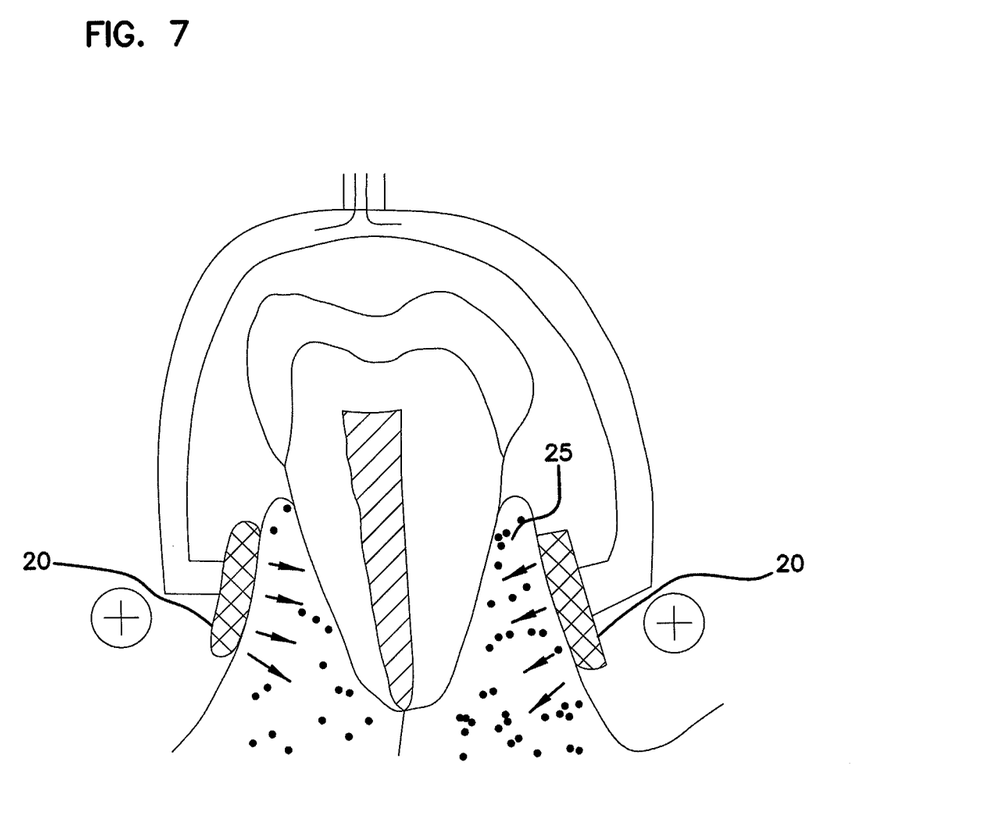
FIG. 7 is an embodiment of the present invention where both the lingual and buccal electrodes are the same charge.

An embodiment of the iontophoretic dental device is shown in FIG. 7. In this embodiment, both electrodes 20 simultaneously contact the buccal and lingual gingiva 25 and are both positively charged. In this embodiment, the positively charged medicament is simultaneously delivered to both the lingual and buccal gingiva.

Figure 8:
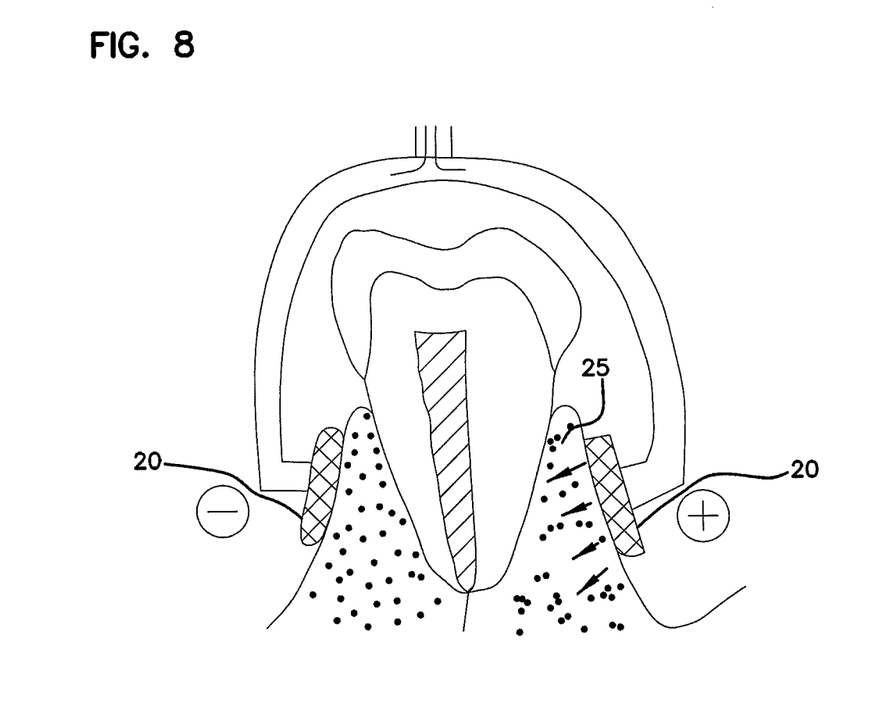
FIG. 8 is an embodiment of the present invention where the lingual and buccal electrodes are opposite charges.

An embodiment of the iontophoretic dental device is shown in FIG. 8. In this embodiment, both electrodes 20 simultaneously contact the buccal and lingual gingiva 25 and are oppositely charged. Therefore, a positively charged medicament is delivered to the buccal gingiva or a negatively charged medicament is delivered to the lingual gingiva. When a positively charged medicament is pushed from the buccal electrode, the negatively charged electrode (lingual) may facilitate the movement by attracting the medicament—and vice versa.

Figure 9:
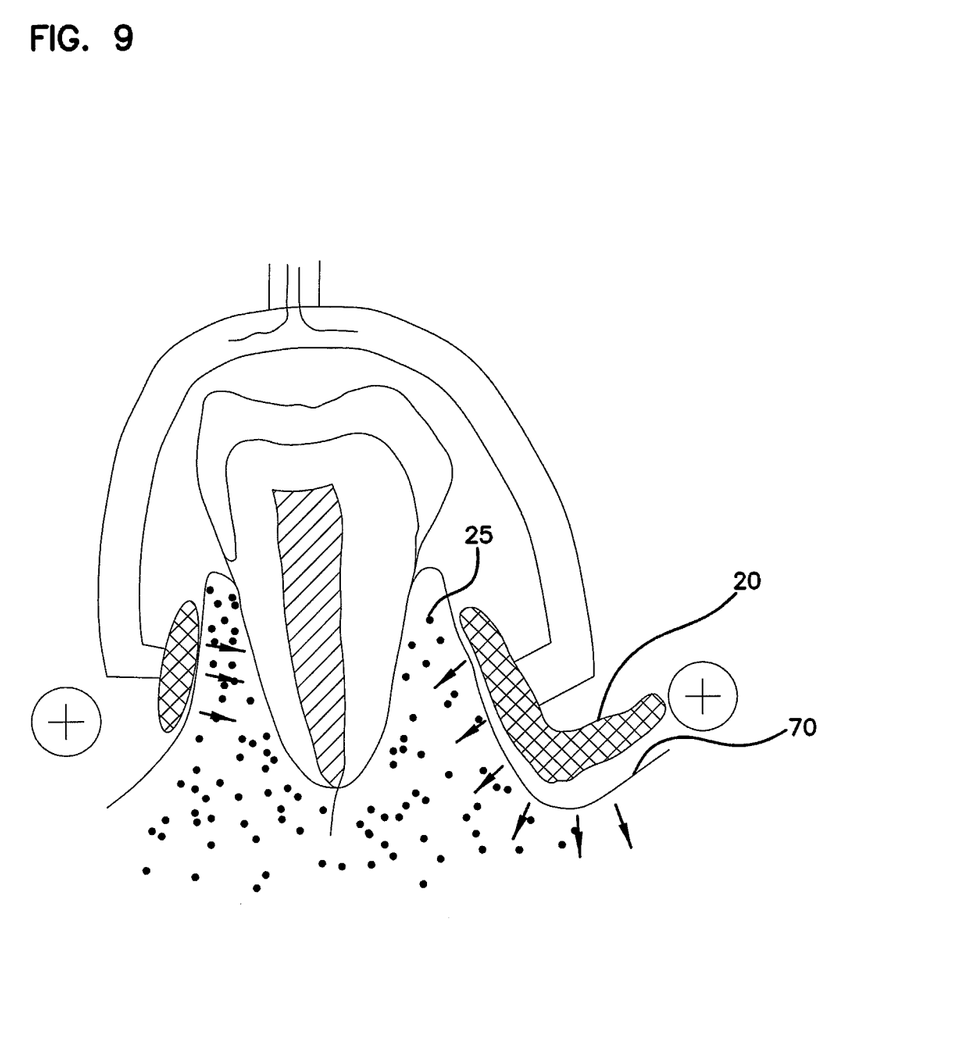
FIG. 9 is an embodiment of the present invention where the lingual and buccal electrodes are the same charge and the buccal electrode is shaped to contact the buccal gingiva and buccal vestibule.

An embodiment of the iontophoretic dental device is shown in FIG. 9. In this embodiment, both electrodes 20 simultaneously contact the buccal and lingual gingiva 25 and are both positively charged. Further, the electrode located at the buccal gingiva is shaped to contact both the buccal gingiva 25 and the buccal vestibule 70. Therefore, the positively charged medicament is simultaneously delivered to the lingual and buccal gingiva 25 as well as the buccal vestibule 70.

Figure 10:
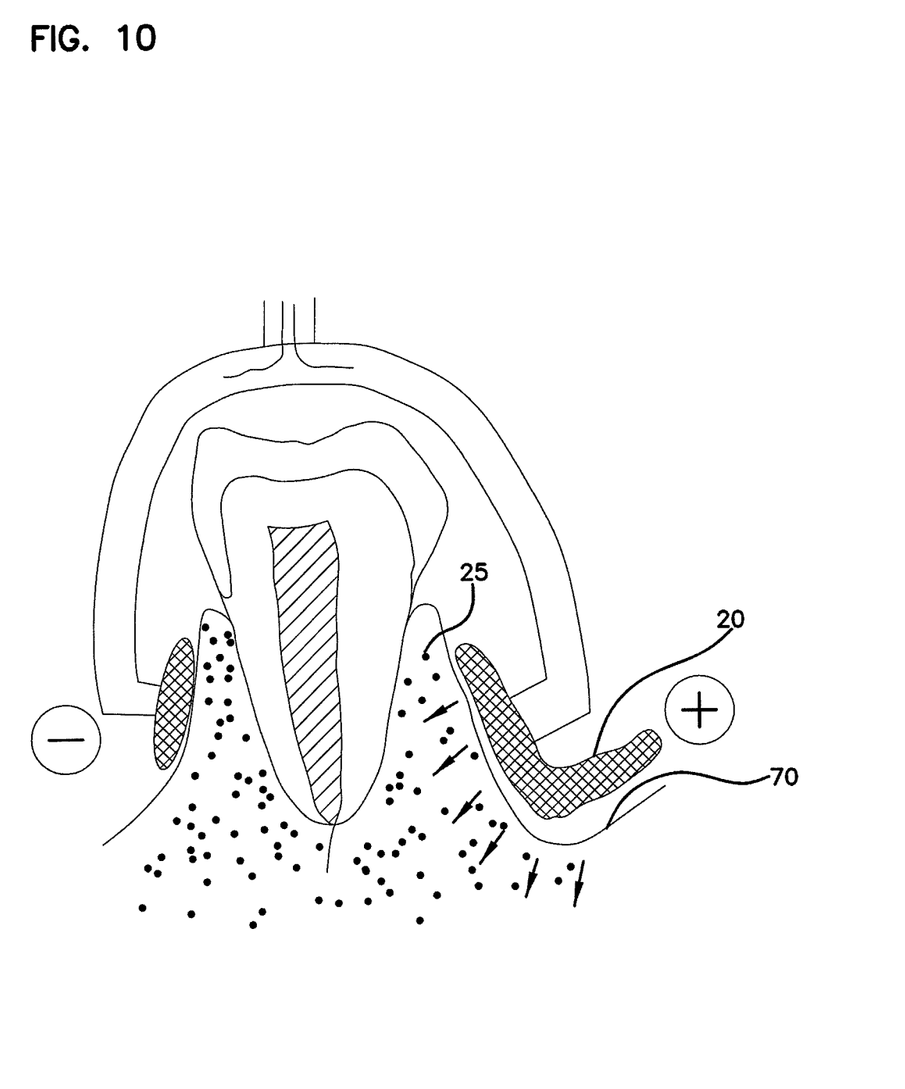
FIG. 10 is an embodiment of the present invention where the lingual and buccal electrodes have opposite charges and the buccal electrode is shaped to contact the buccal gingiva and buccal vestibule.

An embodiment of the iontophoretic dental device is shown in FIG. 10. In this embodiment, both electrodes 20 simultaneously contact the buccal and lingual gingiva 25 and are oppositely charged. Further, the electrode located at the buccal gingiva is shaped to contact both the buccal gingiva 25 and the buccal vestibule 70. Therefore, a positively charged medicament is simultaneously delivered to both the buccal gingiva 25 and the buccal vestibule 70 or a negatively charged medicament is delivered to the lingual gingiva.

The present invention concerns an iontophoretic dental device that positions electrodes at buccal and lingual gingiva, comprising an electrode locating member; and electrodes, wherein the electrodes are operatively attached to the electrode locating member. The electrode locating member may be comprised of different materials, for example, plastic, rubber, aluminum, steel, polymers, or any other material suitable for the uses of this invention. The shape and design of the electrode locating member may take many different shapes or designs that are suitable to position the electrodes at the lingual and buccal gingiva, for example, a horseshoe shape, a C-shape, or an open rectangular shape. The size of the electrode locating member may be variable to fit different size patients, target teeth and gingiva.

The shape and design of the electrodes may also vary. The electrodes may come in varying sizes, for example, x-small, small, medium, large or x-large. In an embodiment, one electrode may be larger than the other. In an additional embodiment, there may be multiple electrodes operatively attached to the electrode locating member and positioned on the buccal and/or lingual side to facilitate the delivery of medicament to a larger area. In a further embodiment, the electrodes are designed to cover quadrants of the mouth, for example, the left, right, upper or lower quadrants. In another embodiment, the electrodes snap on and off the electrode locating member thereby allowing a choice of electrode depending on the application. In some embodiments, the electrodes are purchased already containing specific quantities of medicament, in other embodiments, the medicament is applied to the electrode after purchase.

In an embodiment, the electrode locating member is a clamp. The clamp may be elastic, constructed of a resilient material or include a biasing member (e.g., such as a spring, screw or other member commonly known in the art). In an embodiment, the electrode locating member may be spring loaded.

In an embodiment, the iontophoretic dental device further comprises a coupler to electrically connect the iontophoretic dental device, and a power source and lead wires. The lead wires carry current from the coupler to the electrodes. The coupler may be any device well known in the art to electrically connect a device and power source. In one embodiment it will be a male and female plug/receptacle connector system. The coupler may connect directly at the power source or to a member extending from the power source. The power source may be any number of power sources in the art and are well known to a skilled artisan. The power source may be fixed or portable. The power source may include a battery or a transformed outlet voltage. The power source may be capable of providing constant or alternating current. In an additional embodiment, the power source is capable of accepting feedback from the electrode and adjusting the current dosage (mA*min) accordingly.

Embodiments of the lead wires may be constructed of any wiring suitable for application of the present invention.

Some embodiments of the present invention comprise an iontophoretic dental device where the electrodes at the buccal and lingual gingiva are all positive or negative. This embodiment allows the delivery of a positively or negatively charged medicament to both the lingual and buccal gingiva of the target teeth simultaneously. An additional embodiment may comprise an iontophoretic dental device where the electrodes at the buccal and lingual gingiva of the target teeth are all positive or negative and the dental device further comprises an additional electrode. The additional electrode is placed at an alternative site and is oppositely charged from the electrodes at the buccal and lingual gingiva of the target teeth. The alternative site may be anywhere on the body including the mouth.

Electrodes for other uses in iontophoresis are well known in the art. One embodiment of an electrode in the present invention comprises a conductive layer, an electrolyte reservoir and a membrane. The conductive layer may include metal and/or metal halides. The conductive layer may include inert electrodes like carbon or platinum, reversible electrode like Ag/AgCl electrodes or organic oxidation reduction electrodes like quinine. In one embodiment the conductive layer is carbon based. It may be preferable to evenly distribute the power on the conductive layer.

An electrolyte reservoir of the present invention may be solid, semi-solid, gel, or liquid form. In one embodiment a electrolyte reservoir comprises immobilized ion-exchange resin. The choice of electrolyte reservoir will change depending on the properties and desired charge of the medicament.

The membrane of the electrode may be singular or contain multiple layers. In one embodiment the membrane comprises cotton fabric and gauze matter suitable for oral use. The composition of the membrane will change depending of the composition of the electrolyte reservoir and the charge and properties of the medicament.

In another embodiment, the electrode comprises a gasket that travels along the outside edge of the electrode at the surface where the electrode contacts the gingiva. The gasket may be rubber, plastic or another suitable polymer. The gasket sits at the interface of the electrode and the gingiva of the target teeth to act as a seal.

One aspect of the present invention is an iontophoretic dental system for simultaneously positioning electrodes at the buccal and lingual gingiva of target teeth on which dental work is performed. The electrodes drive the medicament through the gingiva of the target teeth to the root and surrounding tissue and bone of the target teeth. One embodiment comprises a coupler, lead wires and an iontophoretic dental device. The iontophoretic dental device comprises a clamp and electrodes, wherein the electrodes are operatively attached to the clamp. In some embodiments, the iontophoretic dental system further comprises a power source. The system enables the delivery of medicament to the gingiva of target teeth by providing current to the iontophoretic dental device, including the electrodes. The electrode locating member, in some embodiments a clamp, positions the electrodes at the lingual and buccal gingiva of target teeth.

Another aspect of the present invention is a method of delivering a medicament to teeth or surrounding oral tissues by placing an iontophoretic dental device on buccal and lingual gingiva of target teeth and delivering current. The dental device comprises a clamp and electrodes, wherein electrodes are operatively attached to the clamp. The current allows the electrodes to drive the medicament through the gingiva of the target teeth to the root and surrounding tissue and bone of the target teeth. The method may be performed by the patient or a person administering the treatment. In another embodiment, the current is applied prior to placing the iontophoretic dental device on buccal and lingual gingiva of target teeth. Another embodiment includes the method of delivering a medicament to target teeth or surrounding oral tissues by applying the medicament to electrodes, placing an iontophoretic dental device on buccal and lingual gingiva of target teeth and applying current. The device comprising a clamp, and electrodes, wherein electrodes are operatively attached to the clamp and applying current to the electrodes.

Although target teeth are described herein as the target of the medicament, it will be appreciated that a single target tooth or a plurality of target teeth may be medicated in accordance with the principles of the present invention.

The medicament may be applied to the electrode prior to the placement of the iontophoretic dental device on buccal and lingual gingiva of target teeth or after the placement of the iontophoretic dental device on buccal and lingual gingiva of target teeth.

An additional aspect of the present invention is a kit for the delivery of medicament to teeth and surrounding oral tissues, comprising an iontophoretic device. The iontophoretic device comprises an electrode locating member and electrodes, wherein the electrodes are operatively attached to the electrode locating member. In some embodiments the electrodes of the kit come unattached. In some embodiments, the kit comes with multiple electrodes and/or multiple electrode locating members for different patients or uses. In one embodiment, the electrode locating member of the kit is a clamp.

In another embodiment, the kit further comprises a coupler to electrically connect the iontophoretic dental device and power source and lead wires. The lead wires carry current from the coupler to the electrodes. In another embodiment, the kit further comprises a medicament.

The medicament may be come as a solid, gel, solution, or semisolid. The medicament may be a compound, molecule, or treatment that elicits a biological response. For example, a therapeutic agent, pharmaceutical agent, a vaccine, an immunological agent, a local or generic anesthetic or painkiller, such as articaine or novocain, an antigen, or a protein or peptide and antibiotics.

In a preferred embodiment, the medicament will be a solid powder applied to the surface of the electrode. The solid powder may be activated by the addition of a liquid, e.g., saline, saliva, water, or a gel. The liquid may be applied prior to insertion of the iontophoretic device or after the device has been inserted and placed in contact with the gingival.

The powder medicament will be evenly distributed across the electrode for some applications. For other applications the powder medicament may have higher concentrations of medicament at specific areas of the electrode to achieve a more localized effect.

Those skilled in the art will appreciate that the present invention may be embodied by forms that are not disclosed without departing from the spirit or fundamental attributes thereof. The description of the present invention discloses only some embodiments, a skilled artisan understands that other variations are contemplated as being with the scope of the present invention. Accordingly, the present invention is not limited in the particular embodiments which have been described in detail therein. Since many embodiments of the invention can be made without departing from the spirit and scope of the invention, the invention resides in the claims hereinafter appended.

What is claimed is:

1. A method of delivering a medicament to teeth or surrounding oral tissues, comprising:
   (a) placing a first electrode of an iontophoretic dental device on buccal gingiva;
   (b) placing a second electrode of the iontophoretic dental device on lingual gingiva, the iontophoretic dental device comprising: a clamp having a U-shape, the clamp having a first arm and a second arm, wherein the clamp is arranged and configured to be placed over a target tooth with the first arm and the second arm having a length that extends from the top of the target tooth to the buccal and lingual gingiva, respectively, and the first electrode and the second electrode, the first electrode coupled to an end of the first arm and the second electrode coupled to an end of the second arm, wherein the first electrode and the second electrode are positioned on the buccal and lingual gingiva, respectively, to drive a medicament through the buccal and lingual gingiva to a root of the target tooth; and
   (c) applying current to the electrodes.

2. The method of claim 1, wherein the first and second electrodes are positively charged.

3. The method of claim 1, wherein the first and second electrodes are negatively charged.

4. The method of claim 1, wherein the first and second electrodes are oppositely charged.

5. The method of claim 1, wherein the first electrode is shaped to contact the buccal gingiva and buccal vestibule, and wherein placing the first electrode includes placing the first electrode of the iontophoretic dental device on the buccal gingiva and the buccal vestibule.

6. A method of delivering a medicament to teeth or surrounding oral tissues, comprising:
   (a) applying the medicament to electrodes;
   (b) placing a first electrode of an iontophoretic dental device on buccal gingiva;
   (c) placing a second electrode of the iontophoretic dental device on lingual gingiva, the iontophoretic dental device comprising:
   a clamp having a U-shape, the clamp having a first arm and a second arm, wherein the clamp is arranged and configured to be placed over a target tooth with the first arm and the second arm having a length that extends from the top of the target tooth to the buccal and lingual gingiva, respectively, and
   the first electrode and the second electrode, first electrode coupled to an end of the first arm and the second electrode coupled to an end of the second arm, wherein the first electrode and the second electrode are positioned to drive a medicament through the buccal and lingual gingiva to a root of the target tooth; and
   (d) applying current to the electrodes.

7. The method of claim 6, wherein the first and second electrodes are positively charged.

8. The method of claim 6, wherein the first and second electrodes are negatively charged.

9. The method of claim 6, wherein the first and second electrodes are oppositely charged.

10. The method of claim 6, wherein the first electrode is shaped to contact the buccal gingiva and buccal vestibule, and wherein placing the first electrode includes placing the first electrode of the iontophoretic dental device on the buccal gingiva and the buccal vestibule.

* * * * *